United States Patent [19]

Kadell

[11] 4,314,551
[45] Feb. 9, 1982

[54] LARYNGOSCOPE

[76] Inventor: Roger J. Kadell, 508 N. Hunter, Lebanon, Ill. 62254

[21] Appl. No.: 127,925

[22] Filed: Mar. 6, 1980

[51] Int. Cl.³ .............................................. A61B 17/24
[52] U.S. Cl. ...................................... 128/11; 128/16; 128/18
[58] Field of Search ................ 128/10, 11, 15, 16, 128/17, 18, 20

[56] References Cited

U.S. PATENT DOCUMENTS

| 350,809 | 10/1886 | Cole et al. | 128/17 |
| 2,354,471 | 9/1944 | MacIntosh | 128/18 |
| 3,702,606 | 11/1972 | Barnard | 128/17 |
| 3,762,400 | 10/1973 | McDonald | 128/18 |
| 4,052,980 | 10/1977 | Grams et al. | 128/18 |

FOREIGN PATENT DOCUMENTS 2033757  5/1980  United Kingdom ............... 128/17

Primary Examiner—Robert W. Michell
Assistant Examiner—Nancy A. B. Swisher
Attorney, Agent, or Firm—Jerome A. Gross

[57] ABSTRACT

A laryngeal blade useful for displacement of the epiglottis has a fixed blade part projecting from the handgrip and having a tongue-diverting wall which supports a light source projecting toward the forward end of the blade. A movable blade part is hinge-mounted to the fixed blade part at its aft end and extends along the fixed blade part, on its side opposite the tongue-diverting wall, to beyond the end of the fixed blade part. A lever handle fixed to the aft end of the movable blade part is utilized to pivot the movable blade part to displace the epiglottis, exposing the entrance to the trachea, such as for intubation.

1 Claim, 4 Drawing Figures

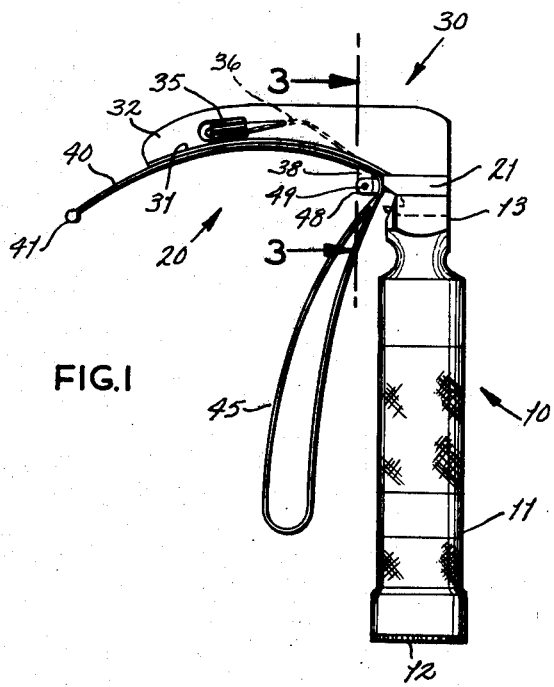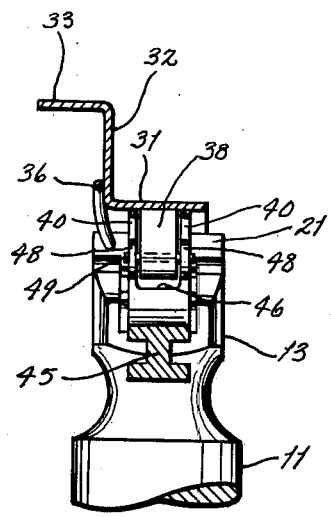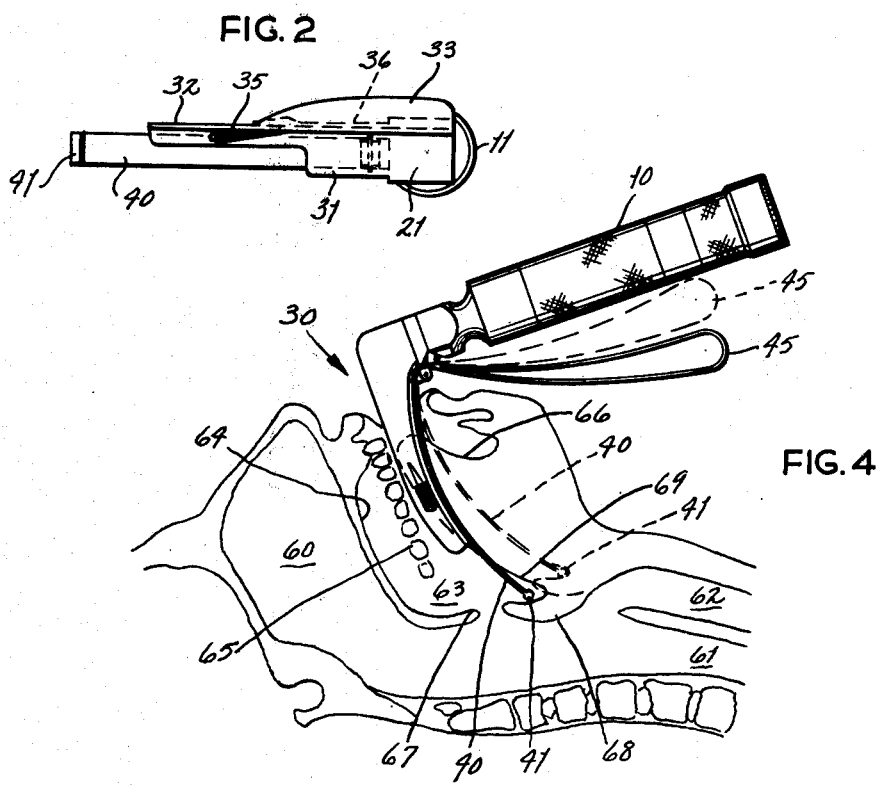

4,314,551

LARYNGOSCOPE

BACKGROUND OF THE INVENTION

The present invention generally relates to laryngoscopes or larynegeal speculums, specifically to laryngeal blades of the type utilized for displacing the epiglottis to expose the entrance to the trachea, such as in intubation.

In the prior art, special instruments called laryngoscopes or laryngeal speculums such as shown in U.S. Pat. No. 2,289,226 to Foregger, are utilized to expose the larynx and epiglottis of asphyxiated or anaesthetized persons. Such instruments have a handgrip from which extends a laryngeal blade carrying a light source. Several types of blades are available, including generally straight blades which are inserted down the side of the oral cavity to the epiglottis, whereby the epiglottis may be displaced in order to permit placement of a tube into the trachea. Another type of blade, which is generally curved and usually is called the MacIntosh blade, having means to divert and hold the tongue to the side to expose the larynx, is inserted in the central part of the oral cavity between the base of the tongue and the epiglottis. By firmly drawing the instrument outward, the tissue superior to the epiglottis and the epiglottis itself may be so displaced as to gain access to the trachea. Inexperienced medical personnel utilizing this type of laryngoscope instead may pivot the blade against the upper front teeth in an unsuccessful attempt to displace the epiglottis, which in extreme cases may result in breaking of those teeth.

SUMMARY OF THE INVENTION

A principal purpose of the present invention is to provide an improved laryngoscope to facilitate displacement of the epiglottis for intubation of asphyxiated or anaesthetized persons. Another object is to provide an improved laryngeal blade which inexperienced medical personnel may employ without damaging the subject's teeth.

Described briefly, an improved laryngeal blade assembly for use with a handgrip is provided with a fixed blade part, projecting from the handgrip, of sufficient length and such curvature to permit extension through the oral cavity to a forward end adjacent the epiglottis; the fixed blade part has a tongue-diverting surface portion extending in a normally vertical plane and supporting a light source projecting toward the forward end of the blade. A movable blade part is mounted by a hinge to the fixed blade part at its aft end on its side opposite the tongue-diverting portion and extends therefrom beyond the forward end of the fixed blade. A lever handle, fixed to the aft end of the movable blade and extending alongside the handgrip, is utilized to pivot the movable blade part against the tissue at the base of the tongue which is superior to the epiglottis, drawing this tissue and, in so doing, drawing and displacing the epiglottis to expose the entrance to the trachea. Its action is in this respect similar to the use of a conventional curved blade type laryngoscope, but it operates without moving the handgrip or fixed blade part.

BRIEF DESCRIPTION OF THE DRAWINGS

FIG. 1 is a side view of the improved laryngeal blade assembly mounted to a conventional handgrip.

FIG. 2 is a view, taken from above, of the laryngeal blade as shown in FIG. 1.

FIG. 3 is a cross-section, taken along line 3—3 of FIG. 1, showing the detail of the hinge connection of the fixed blade part and the movable blade part.

FIG. 4 is a schematic sketch of a section of a human head with the laryngeal blade of FIG. 1 inserted into the oral cavity and showing, in phantom lines, the movable blade displacing the epiglottis.

DESCRIPTION OF THE PREFERRED EMBODIMENT

Described in detail, a preferred embodiment of the present invention utilizes a conventional handgrip, generally designated 10, of the type having an elongated cylindrical handgrip body 11 providing a compartment to contain small dry cell batteries for lighting a lamp on the laryngeal blade, described below. At one of its ends the handgrip body 11 has an openable plate 12 for access to the battery compartment, while at its opposite end it has an upwardly-slotted opening 13 and a pin-mounting provision for the laryngeal blade. The slotted opening 13 has an electrical terminal for connection with a similar terminal on the laryngeal blade.

The improved laryngeal blade assembly, generally designated 20, is mounted to the handgrip 10 by downward-projecting handgrip attachment means 21 received by and snap-locked into the upwardly-slotted opening 13 of the handgrip body 11. The handgrip attachment means 21 has an electrical terminal for connection to the corresponding terminal of the handgrip body 11.

The presently improved laryngeal blade assembly 20 is generally made up of a fixed blade part, generally designated 30, a movable blade part 40 and a lever handle 45 for manipulation of the movable blade part 40. The fixed blade part 30 of the embodiment shown is similar, but not identical, to conventional curved laryngeal blades, and corresponding terms are used hereafter in describing its parts.

The fixed blade part 30 projects outward from the handgrip attachment means 21 generally perpendicular to the handgrip 10. It includes a conventional curved or concave contact portion or wall 31 whose surfaces are generally perpendicular to a normally vertical plane parallel with the handgrip 10 extending in the direction of projection of the blade 20, that is, to the plane of FIG. 1 of the drawing. As best shown in FIG. 2, the concave contact portion 31 ends at its forward or free end in a narrowed portion 34 at one of its sides. The fixed blade part 30 further includes a tongue-diverting portion or wall 32, best seen in FIG. 1, extending perpendicularly from that side of the curved contact portion 31 from which its narrowed portion 34 extends, generally parallel to such normally vertical plane. Projecting from the upper end of the tongue-diverting portion 32 on its upper extremity, shown in FIG. 1, and at the side thereof opposite the curved contact portion 31 as shown in FIG. 3, is a perpendicularly-extending extension or wall 33 along the aft two-thirds of the fixed blade part 30. The vertically-extending tongue-diverter portion 32 carries a light source 35, projecting toward the forward end of the fixed blade part 30 and connected to the batteries within the handgrip 10 by an electrical conductor 36 and the terminals in the handgrip slotted opening 13 and the handgrip attachment means 21. The metal body of the blade and handgrip serve as the common connection for the batteries and light source 35. As best shown in FIG. 3, the lower side of the curved contact portion 31 has, at its connection to the downward-projecting handgrip attachment means 21, a centrally-mounted tubular hinge bushing 38 on an axis perpendicular to such normally vertical plane projecting in the direction of the blade.

The laryngeal blade assembly 20 further includes a curved movable blade part 40 which extends forward, as seen in FIG. 1, beneath the fixed blade part curved contact portion 31 from its hinge bushing 38 to beyond the forward end of the fixed blade part 30, ending in an enlarged rounded tip 41. The curve of the movable blade part 40 conforms to that of the fixed blade contact portion 31.

At the hinge bushing 38, the movable blade part 40 has a generally perpendicular junction with the lever handle portion 45, which extends alongside and normally spaced from the handgrip body 11. The junction of the lever handle 45 and movable blade part 40 has a central opening 46 which is received by the hinge bushing 38 on the fixed blade part 30. At each side of the central opening 46 there is provided an integral hinge lug 48. Connection of the fixed blade part 30 with the movable blade part 40 and its lever handle 45 is by a hinge pin 49 extending through the hinge bushing 38 and lugs 48.

Use of the improved laryngeal speculum is demonstrated in FIG. 4, which shows a rough sketch of the cross-section of a subject's head. The parts shown will be apparent to those familiar with the anatomical structure of the head; the pharynx 60 leads downward into the esophagus 61 at the rear of the neck and to the trachea or windpipe 62 forward of the esophagus 61. The mouth or oral cavity 63 is bounded on its upper side by the upper palate 64 and teeth 65, and at the lower side by the tongue 66 and lower teeth (not shown). At its inner end, the oral cavity 63 is bounded by the uvula 67 on its upper side and by the epiglottis 68 at its lower side, projecting upward at the rear of the tongue 66. Connecting tissue 69 superior to the epiglottis 68 is adjacent to the rear or base of the tongue 66. The epiglottis 68 closes the entrance to the trachea 62 during swallowing; otherwise its upward-extending position hampers insertion of a tube into the trachea 62. This procedure, known as intubation, is utilized in surgery to control respiration or in emergencies to restore proper breathing. Laryngeal speculums, or laryngoscopes, are used in intubation to draw the epiglottis forward, so a tube may be easily inserted.

As shown in FIG. 4, the improved laryngoscope of the present invention may be so utilized to displace the epiglottis 68 forward and downward behind the tongue 66 for insertion of a tube into the trachea 62, but in a unique manner. The procedure requires opening the reclining patient's mouth, drawing the head back, and inserting the laryngeal blade assembly 20, with its movable blade part 40 closed against the curved contact portion 31 of its fixed blade part 30 and its light source 35 energized. The insertion into the oral cavity 63 is with the extension wall 33 toward the upper palate 64; the tongue 66 is pushed sideward by the tongue-diverting portion 32, and held beneath the extension 33. When fully inserted, the rounded tip 41 of the movable blade part 40 is above and between the epiglottis 68 and the anterior side of the tongue 66, against the connecting tissue 69 superior to the epiglottis 68. Finally, when such tube is to be inserted, the lever handle 45 is gently pulled toward the handgrip 10, rotating the movable blade part 40 on the hinge, as shown in phantom lines in FIG. 4, thus drawing it away from the curved contact portion 31 and against the superior tissue 69, drawing it outward generally toward the handgrip 10. This so elevates the connective tissue 69 as to draw the epiglottis 68 itself, generally displacing it in the same direction and gaining access to the trachea 62. Then the tube may be inserted through the oral cavity 63 over the curved contact portion 31 of the fixed blade part 30 and over the movable blade part 40 into the entrance of the trachea 62.

Perhaps the most significant advantage of the improved laryngeal blade is the ease by which medical personnel are trained in its use. Permitting inexperienced medical personnel to use conventional curved-type laryngeal blades to manipulate the epiglottis may result in undesirable pivoting of the blade and at worst may result in breaking out of a subject's upper front teeth. In contrast, use of the improved laryngeal blade of the present invention is thought to be easily learned; the blade is simply inserted through the oral cavity, diverting the tongue to the side until the movable blade portion is adjacent to the epiglottis. Then, without moving the fixed blade part, the movable blade part is rotated by the lever to displace the epiglottis and intubation is then easily performed.

Alternative embodiments and modifications of the present invention are contemplated. Though the above laryngeal blade 20 is designed for use with a conventional battery-pack handgrip, other designs will evolve from provisions of other handgrip means. For example, the laryngeal blade 20 may be provided with a handgrip, either permanent or removable, which extends generally parallel to and aft of the laryngeal blade, rather than generally perpendicular, as in the embodiment shown. This construction is made more practical by the hinged movable blade part of the present invention, for which the blade need not be drawn outward by the perpendicular handle in order to displace the epiglottis, as in prior curved blades. Rather, the fixed blade part of the improved laryngeal blade is not moved during the procedure; only the movable blade part is rotated. As a further alternative, it may be convenient to modify the fixed blade part by changing the length and/or width of its curved contact portion 31 to adapt to the size of the subject's oral cavity and distance from outward of the mouth to the epiglottis; in intubation the tube may then be slided along the upper side of the movable blade part. It may be deemed advantageous to provide a spring acting between the handgrip and the lever handle, or between some other parts, to normally bias the movable blade part against the fixed blade part; this may facilitate ease of insertion of the blade through the oral cavity. From these examples, other modifications may suggest themselves.

I claim:

1. An improved laryngeal speculum of the type inserted into the oral cavity to displace the tongue and raise the epiglottis, comprising
    a hand grip including a source of electrical energy,
    a fixed blade part mounted thereto and of sufficient length and curvature to permit insertion into the oral cavity, and having
    a tongue-diverting wall on one side thereof, and
    an electric light connected to said energy source and directed forwardly,
    in combination with a movable blade part at the side of the fixed blade part which is opposite to the tongue-diverting wall, said movable blade part having a pivot mounting adjacent to the hand grip and an operating lever projecting alongside said hand grip, said movable blade part being formed to follow the curvature of said fixed blade part and extend therebeyond to terminate in a rounded tip, whereby on inserting the rounded tip adjacent to the base of the tongue and squeezing the operating lever against the hand grip, the base of the tongue is raised without raising the laryngoscope or bringing it against the upper teeth and without affecting the direction of the light means.

* * * * *